US009642560B2

(12) United States Patent
Schubert et al.

(10) Patent No.: US 9,642,560 B2
(45) Date of Patent: May 9, 2017

(54) METHOD AND DEVICE FOR DETERMINING THE ORIENTATION OF A CO-ORDINATE SYSTEM OF AN ANATOMICAL OBJECT IN A GLOBAL CO-ORDINATE SYSTEM

(71) Applicant: Brainlab AG, Feldkirchen (DE)

(72) Inventors: Mario Schubert, Poing (DE); Melanie Wegner, Kirchseeon (DE); Sabine Kling, Unterschleißheim (DE)

(73) Assignee: Brainlab AG, Munich (DE)

( * ) Notice: Subject to any disclaimer, the term of this patent is extended or adjusted under 35 U.S.C. 154(b) by 96 days.

(21) Appl. No.: 14/766,471

(22) PCT Filed: Apr. 3, 2013

(86) PCT No.: PCT/EP2013/057024
§ 371 (c)(1),
(2) Date: Aug. 7, 2015

(87) PCT Pub. No.: WO2014/161574
PCT Pub. Date: Oct. 9, 2014

(65) Prior Publication Data
US 2015/0379718 A1 Dec. 31, 2015

(51) Int. Cl.
*G06K 9/00* (2006.01)
*A61B 5/107* (2006.01)
(Continued)

(52) U.S. Cl.
CPC .......... *A61B 5/1072* (2013.01); *A61B 5/1075* (2013.01); *A61B 5/1079* (2013.01);
(Continued)

(58) Field of Classification Search
CPC ..... A61B 34/20; A61B 5/1079; A61B 5/1121; A61B 5/1075; A61B 5/1127;
(Continued)

(56) References Cited

U.S. PATENT DOCUMENTS 6,195,409 B1 * 2/2001 Chang .................. A61B 5/055
378/20
6,302,890 B1 10/2001 Leone, Jr.
(Continued)

FOREIGN PATENT DOCUMENTS

DE     10 311 454       10/2004
DE     10 2007 049 668   4/2009
(Continued)

OTHER PUBLICATIONS

International Search Report and Written Opinion for International Application No. PCT/EP2013/057024 dated Apr. 9, 2014, pp. 6 pages).

*Primary Examiner* — Shefali Goradia
(74) *Attorney, Agent, or Firm* — Tucker Ellis LLP (57) ABSTRACT

A data processing method for determining the relative orientation of an object coordinate system of an anatomical object in a global co-ordinate system, comprising the steps of: acquiring a reference direction dataset representing a first reference direction of a line between a first anatomical landmark of a reference object and a second anatomical landmark of the reference object, and a second reference direction of a line between a third anatomical landmark of the reference object and a fourth anatomical landmark of the reference object, wherein the first and second reference directions are given in a reference coordinate system and the reference object corresponds to the anatomical object; acquiring an object direction dataset representing a first object direction of a line between the first anatomical landmark of the anatomical object and the second anatomical landmark of the anatomical object, and a second object direction of a line between the third anatomical landmark of the anatomical object and the fourth anatomical landmark of the anatomical object, wherein the first and second object directions are given in the global co-ordinate system and the
(Continued)

landmarks of the anatomical object correspond to the landmarks of the reference object; calculating the orientation of the reference co-ordinate system relative to the global co-ordinate system which results in the best match between each of the reference directions and the respectively corresponding object direction; and—using the orientation of the reference co-ordinate system in the global co-ordinate system as the relative orientation of the object co-ordinate system.

16 Claims, 4 Drawing Sheets

(51) Int. Cl.
| | | |
|---|---|---|
| G06T 7/00 | (2017.01) | |
| A61B 5/11 | (2006.01) | |
| G01B 11/14 | (2006.01) | |
| G06K 9/52 | (2006.01) | |
| G06T 3/60 | (2006.01) | |
| G06T 7/60 | (2017.01) | |
| A61B 5/00 | (2006.01) | |
| A61B 34/20 | (2016.01) | |
| A61B 90/00 | (2016.01) | |

(52) U.S. Cl.
CPC .......... *A61B 5/1121* (2013.01); *A61B 5/1127* (2013.01); *A61B 5/7278* (2013.01); *A61B 34/20* (2016.02); *G01B 11/14* (2013.01); *G06K 9/52* (2013.01); *G06T 3/60* (2013.01); *G06T 7/0014* (2013.01); *G06T 7/0024* (2013.01); *G06T 7/0042* (2013.01); *G06T 7/0044* (2013.01); *G06T 7/60* (2013.01); *A61B 2034/2048* (2016.02); *A61B 2034/2055* (2016.02); *A61B 2034/2068* (2016.02); *A61B 2090/3937* (2016.02); *A61B 2562/0219* (2013.01); *G06T 2207/30004* (2013.01); *G06T 2207/30204* (2013.01)

(58) Field of Classification Search
CPC .......... A61B 5/1072; A61B 2034/2055; A61B 2034/2068; A61B 2034/2048; A61B 5/7278; A61B 2090/3937; A61B 2562/021; G06T 7/0044; G06T 7/0042; G06T 7/0014; G06T 7/0024; G06T 7/60; G06T 2207/30204; G06T 2207/30004; G06T 3/60; G01B 11/14; G06K 9/52

See application file for complete search history.

(56) References Cited

U.S. PATENT DOCUMENTS

| | | | |
|---|---|---|---|
| 6,395,005 B1* | 5/2002 | Lovell | A61B 17/1666 606/91 |
| 8,050,473 B2* | 11/2011 | Udupa | G06K 9/6209 378/20 |
| 8,241,296 B2 | 8/2012 | Wasielewski | |
| 8,948,472 B2* | 2/2015 | Wohlgemuth | A61B 6/4476 128/920 |
| 2005/0010106 A1* | 1/2005 | Lang | A61B 6/469 600/425 |
| 2006/0084889 A1 | 4/2006 | Drumm | |
| 2007/0074343 A1 | 4/2007 | McNulty et al. | |
| 2007/0127790 A1* | 6/2007 | Lau | G06F 17/30265 382/128 |
| 2008/0056433 A1 | 3/2008 | Steinle et al. | |
| 2008/0132783 A1 | 6/2008 | Revie et al. | |
| 2008/0212871 A1 | 9/2008 | Dohmen et al. | |
| 2008/0221570 A1 | 9/2008 | Sarin et al. | |
| 2008/0255584 A1 | 10/2008 | Beverland et al. | |
| 2009/0003673 A1 | 1/2009 | Haimerl et al. | |
| 2010/0091951 A1 | 4/2010 | Ngo | |
| 2011/0009778 A1 | 1/2011 | Sarin et al. | |
| 2011/0275957 A1 | 11/2011 | Bhandari | |
| 2012/0283599 A1 | 11/2012 | Borja | |

FOREIGN PATENT DOCUMENTS

| | | |
|---|---|---|
| DE | 10 2007 049 671 | 4/2009 |
| EP | 1 611 863 | 1/2006 |
| EP | 1 905 355 | 4/2008 |
| EP | 1 992 287 | 11/2008 |
| EP | 2 090 228 | 8/2009 |
| EP | 2 168 526 | 9/2011 |
| WO | 2005009303 | 2/2005 |
| WO | 2008153964 | 12/2008 |
| WO | 2009058319 | 5/2009 |
| WO | 2010/145769 | 12/2010 |
| WO | 2011/029466 | 3/2011 |
| WO | 2011/029864 | 3/2011 |
| WO | 2012080840 | 6/2012 |

* cited by examiner

METHOD AND DEVICE FOR DETERMINING THE ORIENTATION OF A CO-ORDINATE SYSTEM OF AN ANATOMICAL OBJECT IN A GLOBAL CO-ORDINATE SYSTEM

RELATED APPLICATION DATA

This application is a national phase application of International Application No. PCT/EP2013/057024 filed Apr. 3, 2013 and published in the English language.

The present invention relates to a data processing method for determining the relative orientation of an object co-ordinate system of an anatomical object in a global co-ordinate system.

Image-guided surgery is proving increasingly popular in improving the precision and success of surgery. Objects to be navigated are provided with references such as marker devices which can be tracked using a medical navigation system, wherein "tracking" means determining the position of the object.

A medical navigation system typically determines the position, i.e. the spatial location and the rotational orientation, of an object, which is quite a complex task. One popular implementation of a medical navigation system uses a stereoscopic camera which captures an image of a marker device which is attached to the object to be tracked. The inventors of the present invention have found that in many applications, the spatial location of an object is less important, such that it is sufficient to determine the orientation of an object, in particular relative to the orientation of another object.

Examples of such applications include hip surgery, in which an implant, such as a cup, is navigated relative to the pelvis, or a biopsy in which the orientation of a biopsy needle relative to a head is tracked. For cup navigation in hip surgery, the parameters of interest are the inclination and anteversion. In a biopsy, the user may be able to find the location of the entry point of the biopsy needle into the head, but require the assistance of the medical navigation system in order to properly align the biopsy needle.

The pelvis and the head are examples of anatomical objects relative to which the orientation of another object is to be tracked or navigated. The relative orientation between the anatomical object and the other object is determined from the orientation of the anatomical object and the orientation of the other object in a global co-ordinate system. Examples of a global co-ordinate system include an Earth-fixed co-ordinate system which can be defined by parameters such as the gravity vector and the magnetic field of the Earth, and an artificial global co-ordinate system which can be defined by field generators which generate a magnetic and/or electric field.

The orientation of an anatomical object in the global co-ordinate system is defined by the orientation of the object co-ordinate system of the anatomical object. The object co-ordinate system is a co-ordinate system which is assigned to the object, preferably in a widely adopted manner such that the orientation of the object co-ordinate system relative to the object is reproducible. The object co-ordinate system is preferably defined by the transverse direction, the longitudinal direction and the sagittal direction.

It is therefore an object of the present invention to provide a method and device for determining the relative orientation of an object co-ordinate system in a global co-ordinate system. This is achieved by the method and device of the independent claims. Advantageous embodiments are defined by the dependent claims.

The present invention relates to a method for determining the relative orientation of an object co-ordinate system of an anatomical object in a global co-ordinate system. The method comprises the step of acquiring a reference direction dataset representing a first reference direction of a line between a first anatomical landmark of a reference object and a second anatomical landmark of the reference object, and a second reference direction of a line between a third anatomical landmark of the reference object and a fourth anatomical landmark of the reference object. The first and second reference directions are given in a reference co-ordinate system which is defined with respect to the reference object.

The reference object corresponds to the anatomical object. The reference object is in particular a scan of the actual anatomical object to be tracked, wherein the scan can be represented by a 3D image dataset of the anatomical object or a generic object, such as an object which is determined from a plurality of sample anatomical objects, for example by averaging a plurality of 3D image datasets of a plurality of sample anatomical objects. The reference object can also be a generic model of the anatomical object. The reference object can thus be a virtual object which is only represented by data. If the reference object is given by image data representing the actual anatomical object, then the reference co-ordinate system is pre-assigned to the reference object, for example in a software which displays the image data on a display device.

The reference object is preferably chosen on the basis of additional information such as the age and/or gender of the patient or the side to be treated.

In general, a direction is defined relative to a corresponding co-ordinate system. This means that the first and second reference directions, for example, are defined relative to the reference co-ordinate system. The actual representation of a direction is unimportant and can for example take the form of angles or a vector.

The next step involves acquiring an object direction dataset representing a first object direction of a line between the first anatomical landmark of the anatomical object and the second anatomical landmark of the anatomical object, and a second object direction of a line between the third anatomical landmark of the anatomical object and the fourth anatomical landmark of the anatomical object. The first and second object directions are given in the global co-ordinate system. The landmarks of the anatomical object correspond to the landmarks of the reference object. This means that for example the term "first landmark" refers to the same landmark on the anatomical object on the one hand and the reference object on the other. Since the landmarks correspond to each other, each of the object directions corresponds to one of the reference directions.

The alignment of the reference co-ordinate system to the reference object is the same as the alignment of the object co-ordinate system to the anatomical object. This means that if the anatomical object and the reference object are identical with respect to at least the first to fourth landmarks, then the reference directions in the reference co-ordinate system equal the object directions in the object co-ordinate system.

The next step of the method involves calculating the orientation of the reference co-ordinate system relative to the global co-ordinate system which results in the best match between each of the reference directions and the respectively corresponding object direction i.e. in other words, the reference directions are orientated in the global co-ordinate system such that they optimally match the object directions. Since the relationship between the reference co-ordinate system and the reference object, and therefore the reference directions, is static, this means that this optimally matched orientation of the reference directions in the global co-ordinate system results in a particular orientation of the reference co-ordinate system in the global co-ordinate system.

In one specific scenario, in which the reference object is in particular an image dataset of the anatomical object or an atlas matched to the anatomical object, there will be one orientation of the reference co-ordinate system for which the reference directions and the object directions form identical pairs. If this is not the case, then the best possible match between the reference directions and the object directions is found. The criteria for the best match can be selected by the skilled person as appropriate, for example in accordance with the desired application. One example of an approach is to calculate the orientation of the reference co-ordinate system relative to the global co-ordinate system such that the sum of the squares of the differences within the pairs of an object direction and a corresponding reference direction is minimised. This is typically referred to as a "least squares" approach.

The next step of the method involves using the orientation of the reference co-ordinate system in the global co-ordinate system as the relative orientation of the object co-ordinate system. As outlined above, the orientation of the reference co-ordinate system relative to the reference object is the same as the orientation of the object co-ordinate system relative to the anatomical object, and the reference directions in the reference co-ordinate system are identical or at least similar to the object directions in the object co-ordinate system, hence if the orientation of the reference directions in the global co-ordinate system is matched to that of the object directions in the global co-ordinate system, then the orientation of the reference co-ordinate system in the global co-ordinate system must be the same as the orientation of the object co-ordinate system in the global co-ordinate system.

The advantage of the present invention is that the object directions can be measured using a simple sensor, such as a gyroscope or a sensor which determines its own position in an electric or magnetic field. There is no need to determine any parameters of the spatial location of the object.

The first anatomical landmark and the third anatomical landmark are preferably identical. This means that the first reference direction and the first object direction relate to a line between the first anatomical landmark and the second anatomical landmark, and the second reference direction and the second object direction relate to a line between the first landmark and the fourth landmark, such that only three different landmarks are used.

The choice of anatomical landmarks defining the reference directions and the object directions can depend on the medical application in question. In an intended hip surgery, the landmarks can depend on the position of the patient. If the patient is in a lateral position, the landmarks can be the ASIS (anterior superior iliac spine) point on the treated side (left or right), the L5 point which is a point on the lowermost lumbar vertebra, and one or more individual points inside the acetabulum. If the patient is in a supine position, the landmarks can be the ASIS point on the treated side, the ASIS point on the non-treated side and one or more individual points inside the acetabulum.

In a preferred embodiment, the object directions are determined from landmark directions. A landmark direction is the direction of a line between a landmark and a common reference point which is none of the landmarks and which is static in the global co-ordinate system. The object direction of a line between two landmarks is calculated from the landmark directions of the respective lines between each of the landmarks and the reference point. This preferred embodiment is particularly advantageous because it is not necessary to access both landmarks at the same time. Instead, they can be accessed consecutively in time.

It should be noted that a landmark may be accessed through the skin without any surgical intervention. If a surgical intervention is required in order to access a landmark, then this surgical intervention is performed in an independent, preceding step which is not part of the present invention. The present invention only relates to processing the data obtained by sampling and not to the sampling process itself.

In a particularly preferred embodiment, a landmark direction is determined by: pointing a light beam, emitted from a light source, at an offset point, wherein the light beam source has a known distance from the landmark and a known orientation relative to the direct line from the light source to the landmark; and acquiring the direction of the light beam and the distance between the light beam source and the offset point. The landmark direction is then calculated from the known distance between the light source and the landmark, the known orientation of the light source relative to the direct line from the light source to the landmark, the direction of the light beam, the distance between the light beam source and the offset point and the offset between the offset point and the reference point, wherein the "offset" refers to the displacement between the offset point and the reference point in up to three spatial dimensions. The offset can be described by an offset direction and an offset distance.

In this embodiment, a quadrilateral is defined by the landmark, the light source, the offset point and the reference point. Since the orientation and length of three of the quadrilateral edges is known, at least the direction of the fourth edge, which is the landmark direction, can be calculated.

The reference point and the offset point are preferably points on a reference device. The reference device is static in the global co-ordinate system. The reference device can for example be a pole or other structure having a spatially extended surface. The reference device preferably comprises at least one label or a surface structure, such that the distance between the offset point and the reference point can be determined with the aid of the label or structure.

In one embodiment, the offset is determined from an image depicting the reference device. The reference point and the offset point can be identified in this image. The offset point is the point at which the light beam is reflected by the reference device. The offset can be determined on the basis of known properties of the camera used to capture the image. The distance between the offset point and the reference point can for example be calculated from the distance between the offset point and the reference point in the image. This distance can alternatively or additionally be calculated from the label on or the structure of the reference device. The camera which captures the image of the reference device can be attached to the light beam source or can be provided independently. Attaching the camera to the light beam source has the advantage that the relative orientation between the camera and the light beam source is known, such that the orientation of the camera, and therefore the orientation of the image, in the global co-ordinate system can be calculated from the orientation of the light beam source.

The offset is preferably determined from the orientation of the reference device in the global co-ordinate system. This orientation can be known, for example because it is vertical, or can be measured using an orientation sensor such as a gyroscope. The offset is then preferably calculated in the global co-ordinate system from the distance between the offset point and the reference point, the orientation of the reference device and the known location of the offset point on the reference device.

In one embodiment, the offset is zero. This means that the light beam points directly at the reference point. The quadrilateral thus becomes a triangle defined by the landmark, the light beam source and the reference point.

In this embodiment, a light beam detector is preferably arranged at the reference point and detects whether or not the light beam hits the reference point. If this is the case, a measurement of the orientation of the light beam source and of the distance between the light beam source and the reference point is automatically triggered.

As outlined above, there are a plurality of approaches for calculating the orientation of the reference co-ordinate system relative to the global co-ordinate system. In one particular approach, the reference co-ordinate system is first orientated such that the plane defined by the reference directions is parallel to the plane defined by the object directions. The reference co-ordinate system and with it, the reference directions is then rotated about an axis perpendicular to the planes, until the best match between the object directions and the reference directions is achieved. The planes can always be made exactly parallel, which includes making the planes identical, even if the reference directions in the reference co-ordinate system and the object directions in the object co-ordinate system do not form identical pairs. Finding the best match in the second step of this approach thus becomes a one-dimensional problem, which makes this approach computationally very effective.

In one embodiment, one or more distances between one of the first, second, third and fourth anatomical landmarks of the anatomical object and another one of these anatomical landmarks of the anatomical object is/are used in the step of calculating the relative orientation of the reference co-ordinate system. This improves the accuracy of the calculation. The actual algorithm which utilises the distances depends on the landmarks and is implemented by the skilled person as appropriate.

In another embodiment, the reference position dataset also represents a third reference direction of a line between the second anatomical landmark of the reference object and the fourth anatomical landmark of the reference object, and the object direction dataset also represents a third object direction of a line between the second anatomical landmark of the anatomical object and the fourth anatomical landmark of the anatomical object. This means that three reference directions are matched to three object directions in the step of calculating the orientation of the reference co-ordinate system relative to the global co-ordinate system, thus resulting in an increased calculation accuracy.

The present invention also relates to a program which, when running on a computer or when loaded onto a computer, causes the computer to perform the method steps of the method described herein and/or to a program storage medium on which the program is stored and/or to a computer on which the program is running or into the memory of which the program is loaded and/or to a signal wave, in particular a digital signal wave, carrying information which represents the program.

The present invention also relates to a device for determining the relative orientation of an object co-ordinate system of an anatomical object in a global co-ordinate system, comprising a computer onto which the aforementioned program is loaded. The computer of this device therefore implements and executes the method described in this document.

In one embodiment, the device also comprises: a registration tool having a body with a landmark point to be held against an anatomical landmark; a light beam source with a known distance from the landmark point and a known orientation relative to the registration tool body; an orientation sensor for determining the orientation of the registration tool in the global co-ordinate system; and a range finder for determining the distance between the light beam source and a point at which the light beam is reflected back towards the registration tool. The information necessary for calculating a landmark direction can be acquired using this registration tool.

The device preferably also comprises a camera which is arranged on the registration tool such that the point at which the light beam is reflected is within the camera's field of view. The camera can thus capture an image from which the offset can be determined.

In one embodiment, the device also comprises a reference device having a reference point. The light beam emitted from the light beam source on the registration tool is to be aimed at the reference device. The reference device preferably also comprises an orientation sensor for determining the orientation of the reference device in the global co-ordinate system.

The reference device preferably has a structure or label which aids in determining the distance between the offset point at which the light beam hits the reference device and the reference point. The orientation of this distance in the global co-ordinate system can then be determined from the orientation of the reference device. The label or structure is for example chequered.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument).

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is in particular known to a navigation system and is for example stored in a computer of the navigation system.

It is the function of a marker to be detected by a marker detection device (for example, a camera or an ultrasound receiver or analytical devices such as CT or MRI) in such a way that its spatial location can be ascertained. The detection device is in particular part of a navigation system. The markers can be active markers. An active marker can for example emit electromagnetic radiation and/or waves which can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

A detection point is in particular a point on the surface of the anatomical structure which is detected, for example by a pointer.

An atlas typically consists of a plurality of generic models of objects, wherein the generic models of the objects together form a complex structure. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service.

In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The method in accordance with the invention is preferably at least partly executed by a computer, i.e. all the steps or merely some of the steps (i.e. less than the total number of steps) of the method in accordance with the invention can be executed by a computer.

It is within the scope of the present invention to combine one or more embodiments and/or options and/or approaches to form a new embodiment wherever this is technically feasible. The aspect of determining an object direction, i.e. the direction of a line between two landmarks, with the aid of landmark directions of the lines between the landmarks and a common reference point can be considered independently from the rest of this document, for example as a separate invention.

The invention shall now be explained in more detail with reference to the accompanying drawings, which show.

Figure 1:
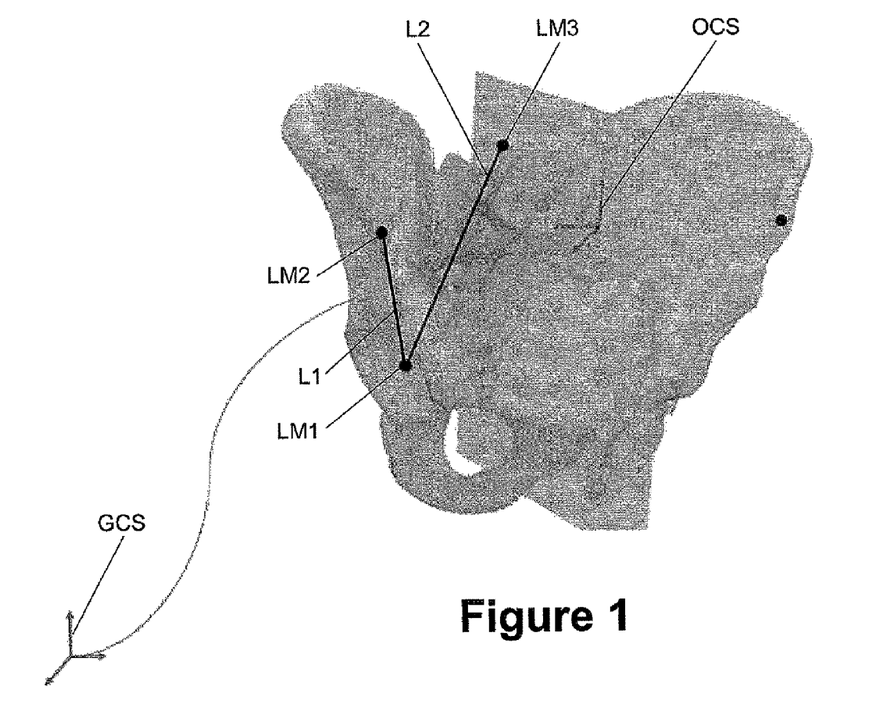
FIG. 1 an anatomical object with landmarks in a global co-ordinate system.

FIG. 1 shows a pelvis 1 as an example of an anatomical object. An object co-ordinate system OCS is virtually associated with the pelvis 1. The goal of the present invention is to determine the relative orientation of the pelvis 1, and therefore of the object co-ordinate system OCS, in a global co-ordinate system GCS. The pelvis 1 comprises a plurality of landmarks, wherein the three distinct landmarks shown in FIG. 1 are a point LM1 inside the acetabulum, an ASIS point LM2 and the L5 point LM3 of the pelvis 1. The landmark LM1 can also be referred to as the fossa point. In order to achieve a consecutive numbering of the landmarks, they are designated as LM1 to LM3 here, contrary to the wording in the claims, wherein LM1 corresponds to the first and third landmark, LM2 corresponds to the second landmark, and LM3 corresponds to the fourth landmark.

The orientation of the object co-ordinate system OCS in the global co-ordinate system GCS cannot be determined directly. An indirect approach is therefore implemented.

This approach utilises a reference object having the same anatomical landmarks LM1, LM2 and LM3 as the anatomical object 1. In this example, the reference object is a generic object which is generated from a plurality of 3D scans of sample anatomical objects of the same type as the anatomical object 1. The scans of the sample anatomical objects are averaged, to determine the generic object. The landmarks can be directly designated in the reference object or independently in each scan of the sample anatomical objects and then averaged over the sample anatomical objects.

A reference direction dataset is acquired which represents a first reference direction of a line between the first anatomical landmark LM1 of the reference object and the second anatomical landmark LM2 of the reference object, and a second reference direction of a line between the first anatomical landmark LM1 of the reference object and the third anatomical landmark LM3 of the reference object. The first and second reference directions are given in a reference co-ordinate system which has the same orientation relative to the reference object as the object co-ordinate system OCS has relative to the anatomical object 1.

An object direction dataset is then acquired which represents a first object direction of a line L1 between the first anatomical landmark LM1 of the anatomical object 1 and the second anatomical landmark LM2 of the anatomical object 1, and a second object direction of a line L2 between the first anatomical landmark LM1 of the anatomical object 1 and the third anatomical landmark LM3 of the anatomical object 1. The first and second object directions are given in the global co-ordinate system GCS.

In the next step, an orientation of the reference object, and therefore of the reference co-ordinate system associated with the reference object, is determined such that the reference directions optimally match the object directions in the global co-ordinate system GCS. In other words, the lines defined by the landmarks of the reference object and the lines defined by the landmarks of the anatomical object should as far as possible form parallel pairs.

Since the reference object and the anatomical object 1 correspond to each other, the virtual orientation of the reference object, and therefore of the reference co-ordinate system, in the global co-ordinate system must match the orientation of the anatomical object 1, and therefore the object co-ordinate system OCS, in the global co-ordinate system GCS. The orientation of the reference co-ordinate system in the global co-ordinate system GCS can thus be used as the relative orientation of the object co-ordinate system OCS in the global co-ordinate system GCS.

If the reference object is a generic object, then it is very unlikely that an exact match between the reference directions and the object directions can be achieved. In this case, the best possible match is determined, wherein the criteria for determining a measure of similarity between the reference directions and the object directions can be set by a skilled person as desired. One suitable approach is a least squares approach which minimises the sum of the squares of the differences between a reference direction and a corresponding object direction for all the directions.

It is difficult to directly determine the object directions because the two landmarks which define a direction have to be accessed simultaneously. An indirect method for determining the object directions is therefore proposed which uses landmark directions. A landmark direction is the direction of a line between a landmark and a common reference point which is none of the landmarks and which is static in the global co-ordinate system GCS.

Figure 2:
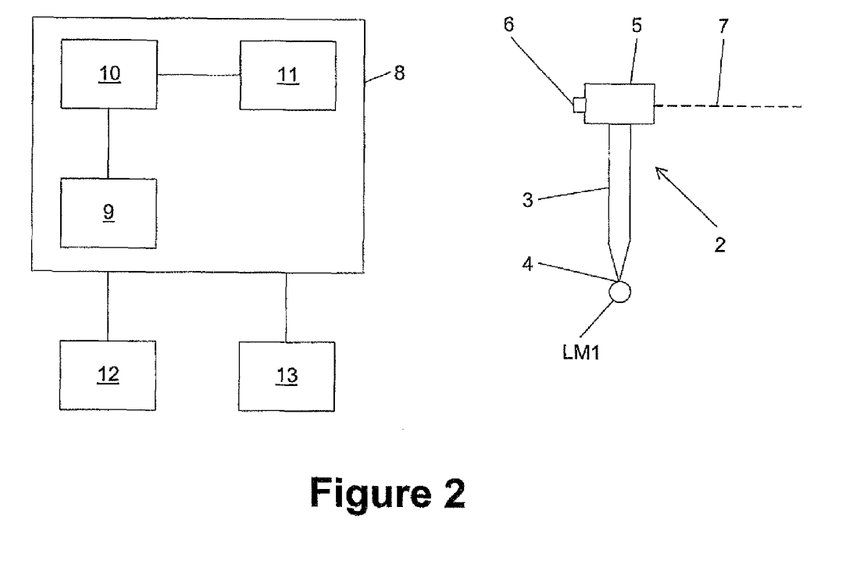
FIG. 2 a system for determining a landmark direction, including a registration tool.

FIG. 2 shows a system for determining a landmark direction. The system comprises a registration tool 2 and a medical navigation system 8.

The registration tool 2 comprises a body 3 with a landmark point 4 to be held against an anatomical landmark, such as the landmark LM1 shown in FIG. 2. A light beam source 5 which is capable of emitting a light beam 7 is rigidly attached to the body 3. The location and orientation of the light beam source 5 on the body 3 is known, such that the distance between the light beam source 5 and the landmark point 4 and the direction of the light beam 7 relative to the body 3 is known. An orientation sensor 6 for determining the orientation of the registration tool 2 in the global co-ordinate system is rigidly attached to the registration tool 2. If the global co-ordinate system is an Earth-fixed co-ordinate system, then the orientation sensor 6 can be a three-axis gyroscope. The orientation sensor 6 is capable of transmitting the determined orientation to the medical navigation system 8.

The medical navigation system 8 comprises a receiving unit 9 for receiving the orientation of the registration tool 2 from the orientation sensor 6, and a central processing unit 10 which is adapted to run a program which implements the method described herein and is connected to the receiving unit 9 in order to receive the orientation of the registration tool 2. The central processing unit 10 is connected to a memory device 11 in which the program and/or data for performing the method is/are stored.

The navigation system also comprises an input unit 12 for receiving information and an output unit 13 for displaying information.

Figure 3:
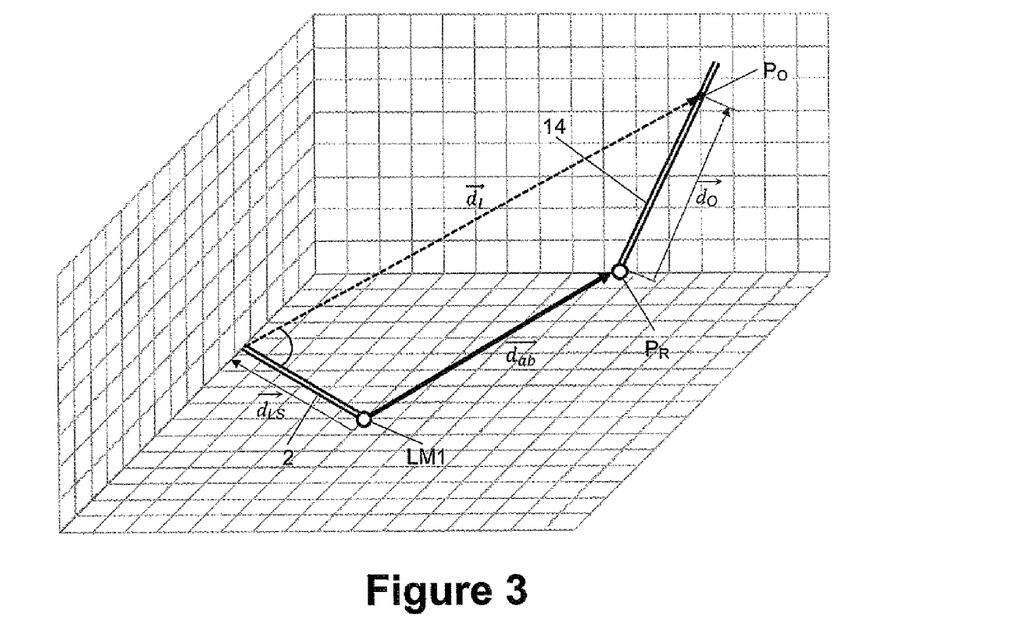
FIG. 3 a geometry for determining a landmark direction.

The principle of determining a landmark direction is explained with reference to FIG. 3. As shown in this figure, the landmark point 4 of the registration tool 2 is held at the landmark LM1, and a reference device 14 is provided such that it is static in the global co-ordinate system GCS. The orientation of the reference device 14 is either known and provided to or stored in the medical navigation system 8 or is determined using an orientation sensor (not shown) and sent to the medical navigation system 8. A reference point $P_R$ is defined on the reference device 14.

In the present example, the light beam source 5 is a laser range finder which is capable of determining the distance between the laser range finder 5 and a point at which the laser beam 7 is reflected. It is also capable of transmitting the acquired distance to the medical navigation system 8 via the receiving unit 9.

The registration tool 2 is held such that the light beam 7 hits the reference device 14. The point at which the light beam 7 hits the reference device 14 and is reflected back to the registration tool 2 is referred to as the offset point $P_O$. Since the orientation of the light beam source 5 can be measured using the orientation sensor 6, and the distance between the offset point $P_O$ and the light beam source 5 can be measured, the medical navigation system 8 can calculate the vector $d_l$ from the light beam source 5 to the offset point $P_O$. As can be seen from FIG. 3, the light beam source 5, the landmark LM1, the offset point $P_O$ and the reference point $P_R$ constitute a quadrilateral. The vector $d_{ab}$ from the landmark LM1 to the reference point $P_R$ is the landmark direction which belongs to the landmark LM1. This vector can be calculated if enough information about the quadrilateral is available.

The vector $d_{ls}$ from the landmark LM1 to the light source 5 can be calculated from the known relative position between the light source 5 and the landmark point 4 in combination with the orientation of the registration tool 2 as determined using the orientation sensor 6. The offset vector $d_O$ can be calculated from the orientation of the reference device 14 and the location of the offset point $P_O$ on the reference device 14. This location can be determined automatically, for example by a camera which captures an image of the reference device 14 and calculates the location by identifying the offset point $P_O$ in the image, or manually by an operator who identifies the location of the offset point $P_O$ on the reference device 14 and inputs this information into the medical navigation system 8 using the input unit 12.

Once the vectors $d_{ls}$, $d_l$ and $d_O$ are known, the vector $d_{ab}$ representing the landmark direction of the first landmark LM1 can be calculated.

Two landmarks together with the reference point $P_R$ constitute a triangle. If the vectors from the two landmarks to the reference point $P_R$ are respectively known, then the direction of the line between the two landmarks can be calculated in the global co-ordinate system GCS, hence if the landmark directions of all three landmarks LM1, LM2 and LM3 are known, then all the object directions in the global co-ordinate system GCS can be calculated.

The present example relates to a scenario in which the object directions of two lines, one between a first landmark and a second landmark and another between the first landmark and a third landmark, is utilised. It is however possible to use object directions and reference directions defined by two pairs of landmarks, wherein no landmark is common to both pairs of landmarks.

In this example embodiment, the orientation of the reference co-ordinate system in the global co-ordinate system is calculated in two steps. In the first step, the plane spanned by the reference directions is made parallel to the plane spanned by the object directions. The reference object, and therefore the reference co-ordinate system, is then rotated about an axis perpendicular to these planes until the best match between the object directions and the reference directions is achieved.

Alternatively, the reference co-ordinate system can first be aligned in the global co-ordinate system GCS such that one of the reference directions equals the corresponding object direction. The reference co-ordinate system is then rotated about this direction until the other reference direction(s) optimally match/es the other object direction(s), respectively.

In another alternative approach, the length of the offset vector $D_O$ is set to zero by pointing the light beam 7 directly at the reference point $P_R$. In this case, the quadrilateral becomes a triangle, and the vector $d_{ab}$ can be calculated from the vectors $d_{ls}$ and $d_l$. Utilising an offset can however be advantageous if the scope for orientating the registration tool 2 is limited, such that it may not be possible to aim the light beam 7 directly at the reference point $P_R$. The offset point $P_O$ can be different for the different landmark directions determined, which makes the approach more flexible.

Preferably, the reference direction dataset is based on additional information such as the gender of the patient to whom the anatomical object belongs and/or the side (left or right) of the landmarks of the anatomical object.

Figure 4:
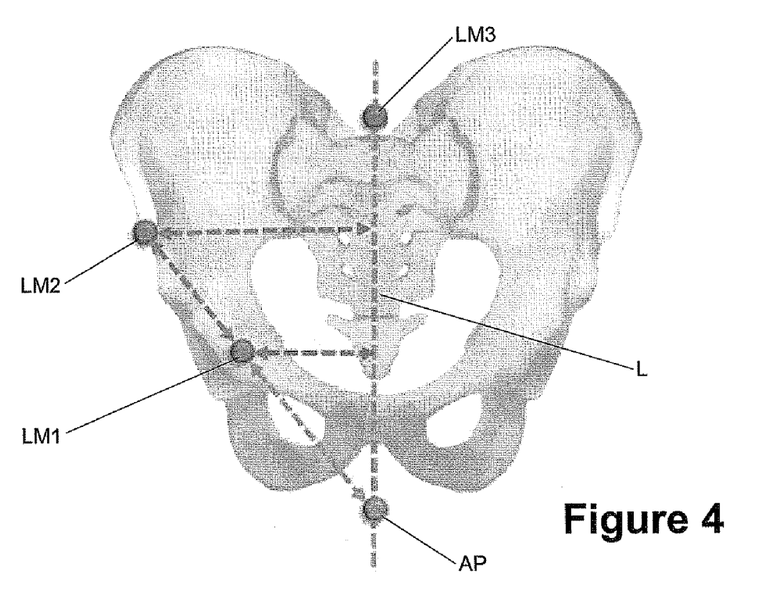
FIG. 4 an auxiliary point being determined.
Figure 5:
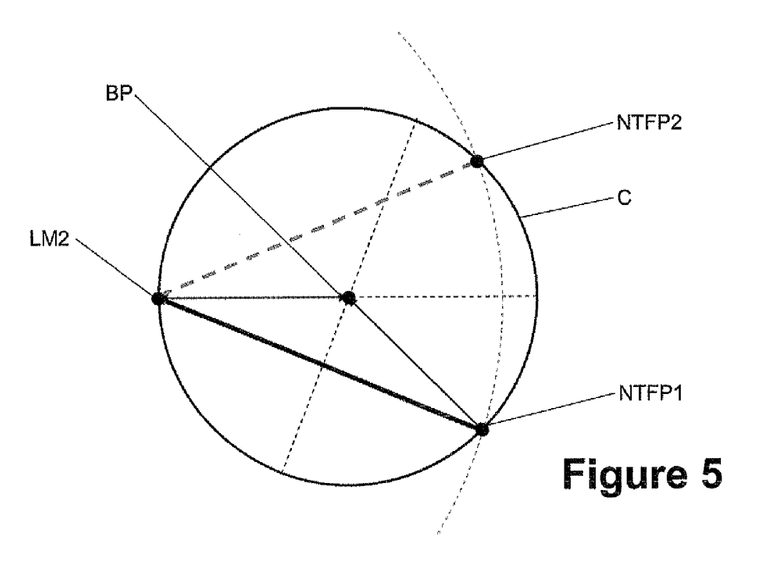
FIG. 5 the transverse direction of the reference co-ordinate system being determined.

Another approach for calculating the orientation of the reference co-ordinate system relative to the global co-ordinate system GCS is shown with reference to FIGS. 4 and 5, wherein the landmarks LM1, LM2 and LM3 are still the fossa point, the ASIS point and the L5 point, respectively. This approach utilises the distance between the landmarks LM1 and LM2.

The landmark LM3 is known to lie in the mid-sagittal plane of the patient. A first part of this approach involves determining an auxiliary point AP which also lies in the mid-sagittal plane. This point is defined as shown in FIG. 4.

The directions and distances between the landmarks LM1 and LM2 (the first reference direction) and the landmarks LM1 and LM3 (the second reference direction) are respectively known. In this approach, the distance between the two ASIS points, i.e. the left and right ASIS points, is known, for example from having been measured. The distance from the landmark LM2 to the mid-sagittal plane is thus half of this ASIS-ASIS distance.

The distance between the landmark LM1 and the corresponding (symmetrical) fossa point is also known, for example from having been measured or from statistical data. The distance from the landmark LM1 to the mid-sagittal plane is thus half of this fossa-fossa distance. By applying the theorem on intersecting lines to the situation shown in FIG. 4, the location of the auxiliary point AP relative to the landmarks LM1, LM2 and LM3 is calculated. A line L is then defined which passes through the auxiliary point AP and the landmark LM3. This line L must lie in the mid-sagittal plane and thus defines a first direction which can be used to determine the orientation of the reference co-ordinate system. However, the rotational alignment of the mid-sagittal plane about the line L is not yet known.

In the next step, the base point BP of a projection of the landmark LM2 onto the line L is calculated. The base point BP is the point on the line L with the shortest possible distance from the landmark LM2. A circle C is then calculated which has this base point BP as its centre and a radius which corresponds to the distance between the base point BP and the landmark LM2, wherein the line L is perpendicular to the plane of the circle C. The landmark LM2 thus lies on the circle C. The circle C is shown in FIG. 5.

Since the pelvis is considered to be mirror-symmetrical, the landmark LM2 must have a corresponding fossa point on the other side of the pelvis at the same distance from the mid-sagittal plane. The line which connects the landmark LM2 and the other, symmetrical fossa point must define the transverse direction of the pelvis and thus enable the second of the three directions of the orientation of the reference co-ordinate system in the global co-ordinate system GCS to be calculated.

Since the fossa-fossa distance is known, there are only two points on the circle C which could be the symmetrical fossa point. As shown in FIG. 5, those two points are defined by the intersections between the circle C and another circle which has the point LM2 as its centre and the fossa-fossa distance as its radius and which lies in the same plane as the circle C. These two points are referred to as NTFP1 and NTFP2, where NTFP stands for Non-Treated side Fossa Point.

Prior knowledge about the landmarks is used to resolve this ambiguity. The landmark LM3 is known to be very posterior, while an ASIS point is known to be very anterior. The correct NTFP is therefore the more anterior one, which is NTFP 1. The orientation of the mid-sagittal plane in the global co-ordinate system GCS is then known.

The last degree of freedom of the reference co-ordinate system in the global co-ordinate system is the rotational alignment about the transverse (left-right) direction. How this degree of freedom is determined depends on the available landmarks. Many possible approaches use the frontal pelvis plane, which is a frontal plane comprising the ASIS points, i.e. the landmark LM2 in the present example. One option is to align the reference co-ordinate system such that the angle between the frontal pelvis plane and a plane defined by the two ASIS points and the deepest point in the acetabulum equals a reference angle. Another option is to align the reference co-ordinate system such that the angle between the frontal pelvis plane and a plane defined by the two ASIS points and the centre of the acetabulum equals a reference angle. Yet another option is to align the reference co-ordinate system such that the distance between the frontal pelvis plane and an anterior point on the acetabular rim equals a reference distance. A fourth option is to align the reference co-ordinate system such that the angle between the frontal pelvis plane and a line passing through the landmark LM3 and the auxiliary point AP equals a reference angle. The reference angle(s) and/or reference distance are preferably based on statistical data, optionally in combination with other information such as the gender of the patient. Two or more of these options can be combined if the required values are available.

The invention claimed is:

1. A data processing method for determining the relative Orientation of an object co-ordinate system of an anatomical object in a global co-ordinate system, comprising:
   acquiring a reference direction dataset representing a first reference direction of a line between a first anatomical landmark of a reference object and a second anatomical landmark of the reference object, and a second reference direction of a line between a third anatomical landmark of the reference object and a fourth anatomical landmark of the reference object, wherein the first and second reference directions are given in a reference co-ordinate system and the reference object corresponds to the anatomical object;
   acquiring an object direction dataset representing a first object direction of a line between the first anatomical landmark of the anatomical object and the second anatomical landmark of the anatomical object, and a second object direction of a line between the third anatomical landmark of the anatomical object and the fourth anatomical landmark of the anatomical object, wherein the first and second object directions are given in the global co-ordinate system and the landmarks of the anatomical object correspond to the landmarks of the reference object;
   calculating the orientation of the reference co-ordinate system relative to the global co-ordinate system which results in the best match between each of the reference directions and the respectively corresponding object direction; and
   using the orientation of the reference co-ordinate system in the global co-ordinate system as the relative orientation of the object co-ordinate systems, wherein the object directions are determined from landmark directions, wherein a landmark direction is the direction of a line between a landmark and a common reference point which is none of the landmarks and which is static in the global co-ordinate system.

2. The method according to claim 1, wherein a landmark direction is determined by:
   pointing a light beam, which is emitted from a light beam source, at an offset point, the light beam source having a known distance from the landmark and a known orientation relative to the direct line from the light source to the landmark;
   acquiring the direction of the light beam;
   acquiring the distance between the light beam source and the offset point; and
   calculating the landmark direction from the known distance between the light source and the landmark, the known orientation of the light source relative to the direct line from the light source to the landmark, the direction of the light beam, the distance between the light beam source and the offset point and the offset between the offset point and the reference point.

3. The method according to claim 2, wherein the reference point and the offset point are points on a reference device.

4. The method according to claim 3, wherein the offset is determined from an image depicting the reference device.

5. The method according to claim 3, wherein the offset is determined from the orientation of the reference device in the global co-ordinate system.

6. The method according to claim 2, wherein the offset is zero.

7. The method according to claim 1, wherein in the step of calculating the relative orientation of the reference co-ordinate system, the reference co-ordinate system is first orientated such that the plane defined by the reference directions is parallel to the plane defined by the object directions, and the reference co-ordinate system is then rotated about an axis perpendicular to the planes, until the best match is achieved.

8. The method according to claim 1, wherein one or more distances between one of the first, second, third and fourth anatomical landmarks of the anatomical object and another one of these anatomical landmarks of the anatomical object is/are used in the step of calculating the relative orientation of the reference co-ordinate system.

9. The method according to claim 1, wherein the reference position dataset also represents a third reference direction of a line between the second anatomical landmark of the reference object and the fourth anatomical landmark of the reference object, and the object direction dataset also represents a third object direction of a line between the second anatomical landmark of the anatomical object and the fourth anatomical landmark of the anatomical object.

10. A program embodied on a non-transitory computer readable medium which, when running on a computer or when loaded onto a computer, causes the computer to perform steps of:
   acquiring a reference direction dataset representing a first reference direction of a line between a first anatomical landmark of a reference object and a second anatomical landmark of a reference object, and a second reference direction of a line between a third anatomical landmark of the reference object and a fourth anatomical landmark of the reference object, wherein the first and second reference directions are given in a reference co-ordinate system and the reference object corresponds to the anatomical object;
   acquiring an object direction dataset representing a first object direction of a line between the first anatomical landmark of the anatomical object and the second anatomical landmark of the anatomical object, and a second object direction of a line between the third anatomical landmark of the anatomical object and the fourth anatomical landmark of the anatomical object, wherein the first and second object directions are given in the global co-ordinate system and the landmarks of the anatomical object correspond to the landmarks of the reference object;
   calculating the orientation of the reference co-ordinate system relative to the global co-ordinate system which results in the best match between each of the reference directions and the respectively corresponding object direction; and
   using the orientation of the reference co-ordinate system in the global co-ordinate system as the relative orientation of the object co-ordinate system,
   wherein the object directions are determined from landmark directions, wherein a landmark direction is the direction of a line between a landmark and a common reference point which is none of the landmarks and which is static in the global co-ordinate system.

11. A device for determining the relative orientation of an object co-ordinate system of an anatomical object in a global co-ordinate system, comprising a computer onto which the program according to claim 10 is loaded.

12. The device according to claim 11, further comprising:
   a registration tool having a body with a landmark point to be held against an anatomical landmark;
   a light beam source with a known distance from the landmark point and a known orientation relative to the registration tool body;

an orientation sensor for determining the orientation of the registration tool in the global co-ordinate system; and a range finder for determining the distance between the light beam source and a point at which the light beam is reflected back towards the registration tool.

13. The device according to claim 12, further comprising a camera which is arranged on the registration tool such that the point at which the light beam is reflected is within the camera's field of view.

14. The device according to claim 12, further comprising a reference device having a reference point and an orientation sensor for determining the orientation of the reference device in the global co-ordinate system.

15. A program storage medium on which the program of claim 10 is stored and/or a computer on which the program of claim 10 is running or into the memory of which the program is loaded.

16. A computer comprising:
a non-transient memory storing the program of claim 10; and
a processor executing the program.

* * * * *